United States Patent [19]

Spencer

[11] Patent Number: 4,988,296

[45] Date of Patent: Jan. 29, 1991

[54] MEDICAL APPLIANCE HOLDER

[76] Inventor: Charles M. Spencer, 2713 Prince Cir., Tuscaloosa, Ala. 35401

[21] Appl. No.: 220,453

[22] Filed: Jul. 15, 1988

[51] Int. Cl.$^5$ .............................................. A61C 3/00
[52] U.S. Cl. .................................. 433/163; 433/229; 2/168; 128/852
[58] Field of Search ...................... 433/49.2, 163, 229, 433/25; 2/160, 168, DIG. 7; 206/63.5; 128/852, 879, 361, 329; 604/292; 606/125

[56] References Cited

U.S. PATENT DOCUMENTS

| 334,513 | 1/1886 | Cole | 2/160 |
|---|---|---|---|
| 3,298,368 | 1/1967 | Charos | 604/292 |
| 3,362,408 | 1/1968 | Stocki et al. | 606/125 |
| 4,198,985 | 4/1980 | Abel | 128/329 R |
| 4,245,656 | 1/1981 | Farr et al. | 2/160 |
| 4,447,912 | 5/1984 | Morrow | 2/160 |

Primary Examiner—Cary E. Stone
Attorney, Agent, or Firm—Jennings, Carter, Thompson & Veal

[57] ABSTRACT

An appliance for use by medical and dental practitioners utilizes a latex glove as a platform for attachment of supplies. After donning a pair of latex gloves, the practitioner may load a measured portion of dentifrice into a suitable receptacle. The receptacle may then be detachably affixed to the glove surface in a location permitting convenient access to the dentifrice retained therein. After completion of the procedure the gloves and affixed receptacle may be removed and disposed of as a unit. In a simple embodiment of the appliance a pouch or depression formed on the glove surface serve as dentifrice receptacles.

16 Claims, 2 Drawing Sheets

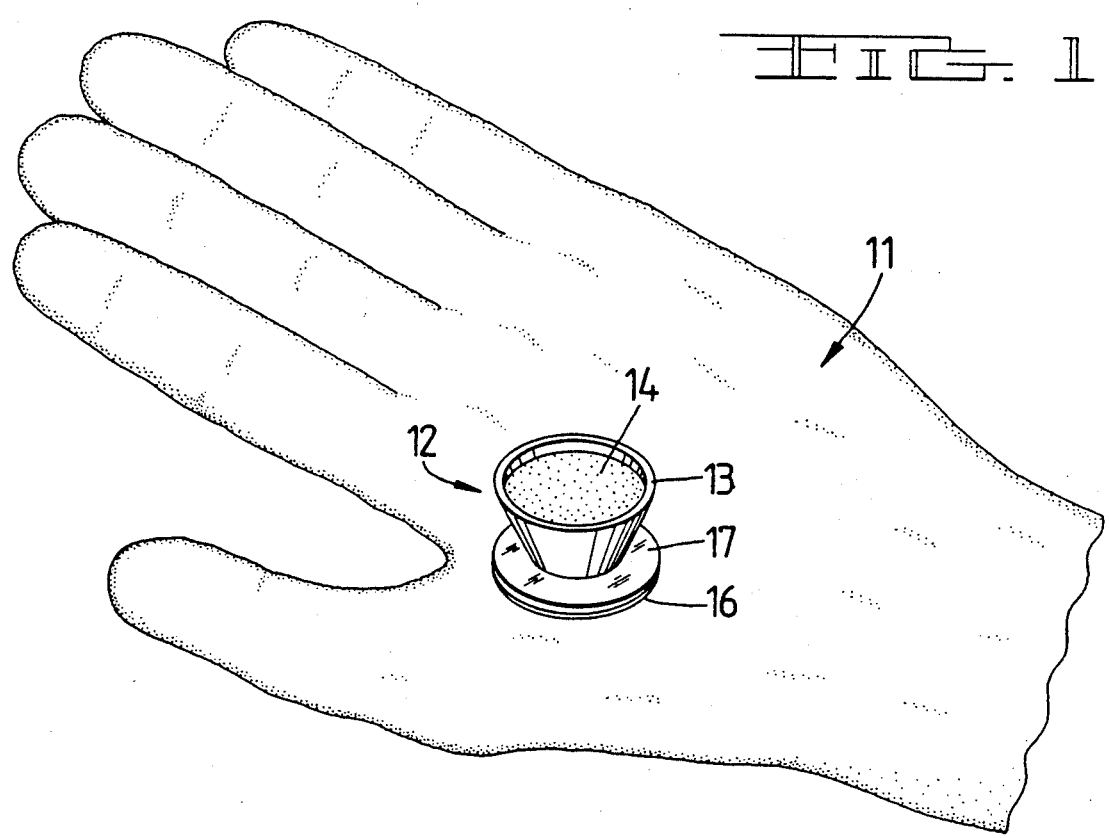
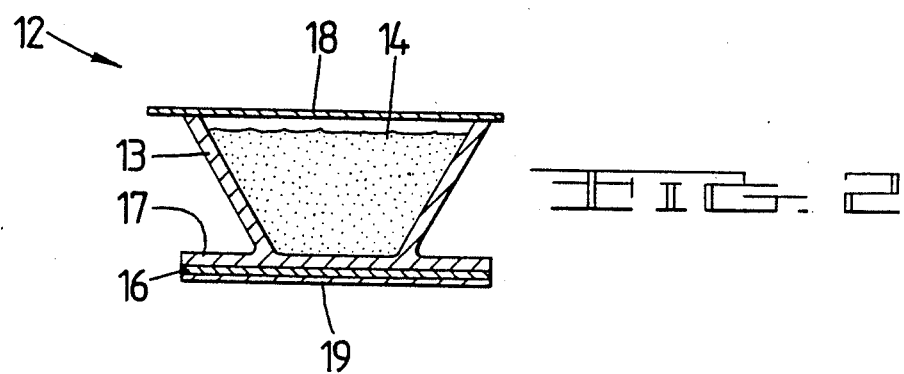
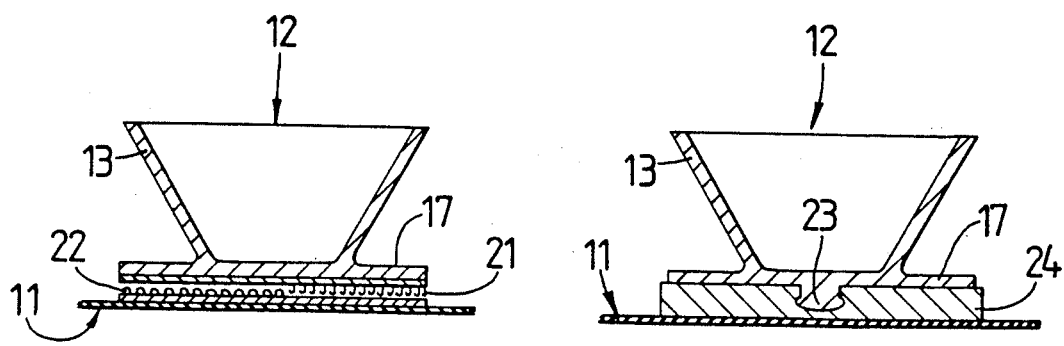

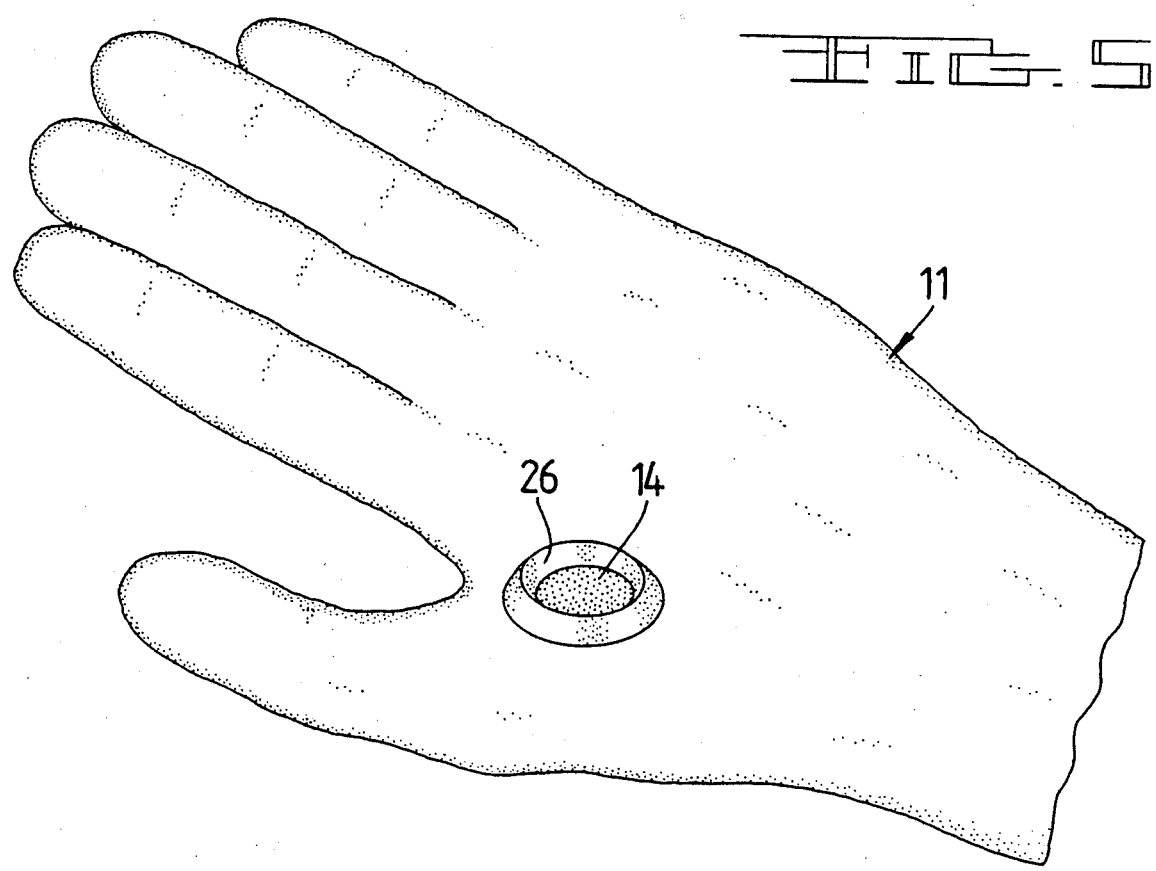
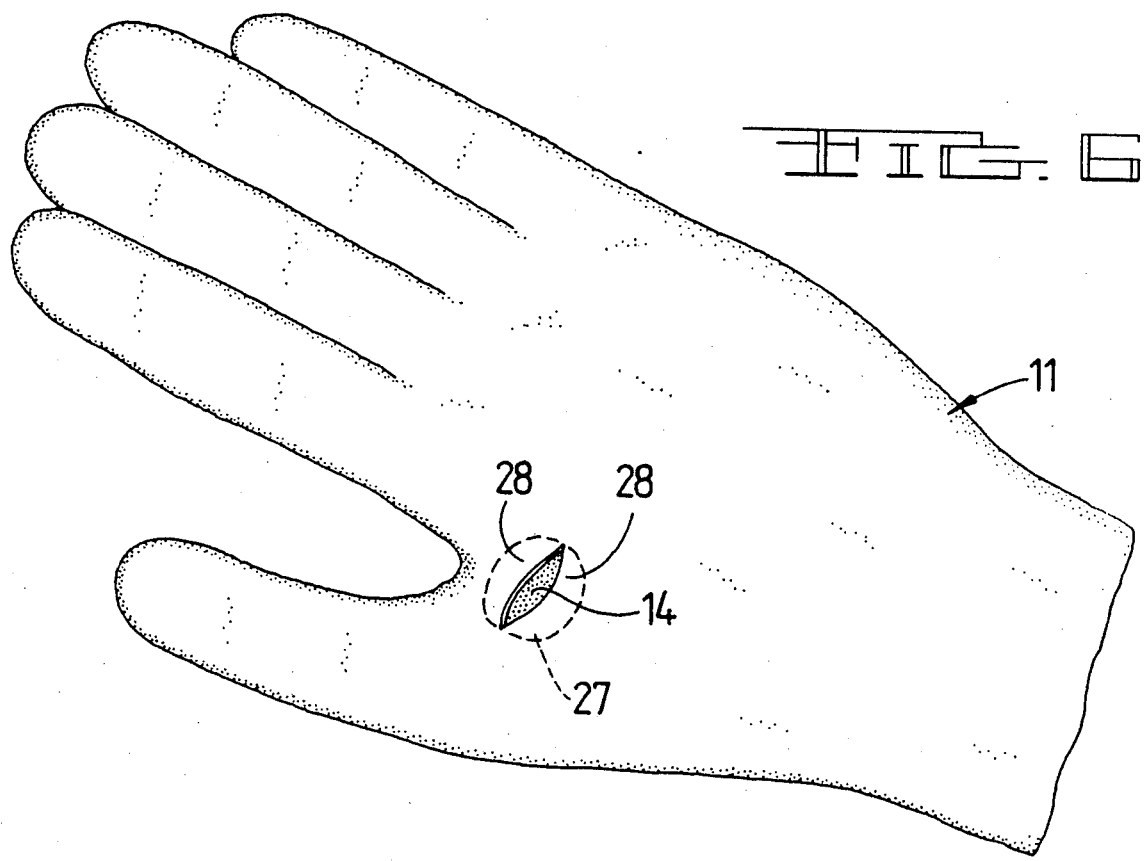

MEDICAL APPLIANCE HOLDER

FIELD OF THE INVENTION

The present invention relates generally to the field of medical care and more particularly to dental appliances. Even more particularly, the present invention relates to a system whereby dental appliances and the like may be detachably affixed to the latex gloves worn by an attending dentist while performing dental procedures.

BACKGROUND OF THE INVENTION

Traditional sterile technique requires that all personnel contacting patients don protective clothing as a barrier against pathogenic cross-contamination. Protective masks, gloves and clothing covers are used in most, if not all, surgical procedures. However, the dental profession traditionally has foregone the use of protective clothing and gloves in most procedures involving patient contact The necessity of working and manipulating instruments within the close confines of the mouth, as well as a lower probability of dangerous cross-contamination, made the wearing of barrier clothing impracticable.

The advent of acquired immune deficiency syndrome (AIDS) has forced the dental profession to re-examine the value of protective clothing in procedures involving patient contact. Research has indicated that the viral pathogens causing AIDS are transmitted via contact with body fluids, including blood and possibly saliva. To avoid contamination from the AIDS virus, dental practitioners in increasing numbers are donning latex gloves, despite the resultant loss in dexterity.

The hindrance of latex gloves has added to the difficulty of many common dental procedures. The cleaning of teeth (dental prophylaxIs) is a typical example. In early procedures the tooth cleaning agent (prophylaxis paste) was taken from a bulk package and placed on a tray suspended above the reclining patient. The paste was then repeatedly transferred as needed to the teeth using a rotary, hand-held cleaning device. To simplify the procedure many dentists made use of a metal dispensing instrument consisting of two C-shaped half loops affixed perpendicularly to one another. One loop encircled the index finger of the user, while the other loop accepted a unit of prophylaxis paste. The above described dispensing system operates efficiently when attached to a bare index finger, but use on a gloved hand makes attachment and removal of the instrument cumbersome at best.

SUMMARY OF THE INVENTION

It is an object of the present invention to provide a simple system for retention of dental appliances. It is a further object of the present invention to provide a convenient appliance for detachably affixing dental appliances to latex gloves.

To accomplish these objects I have utilized the latex glove itself as a Platform for attaching dental tools and supplies. In one form, mY invention comprises a deformable, cup-like receptacle which attaches to the exposed outer surface of a latex glove. A suitably sized adhesive patch mounted on the underside allows the user to position the receptacle at any convenient location on the glove. Prophylaxis paste or any dental supply item may be loaded in the receptacle and easily accessed during the dental procedure. After procedure completion, the entire unit (glove and receptacle structure) may be removed as a unit for disposal. The deformable receptacle structure eases removal.

In an alternate embodiment, a flat, deformable base may be affixed to the underside of the receptacle. The base stabilizes the structure and provides a more secure attachment structure for the adhesive patch.

If the user does not wish to load the receptacle from a bulk jar of prophylaxis paste prior to each administration, the receptacle unit may be pre-packaged with a measured unit of paste. A thin, peel-off coverlet stretched over the receptacle opening maintains paste sterilitY until immediately prior to administration. Alternatively, currently available sterile unit packages of prophylaxis paste may be adhesively affixed to the glove surface.

I envision many different means for attaching the above described receptacle or flat base to the glove surface. As noted above, an adhesive patch may be affixed on the receptacle underside or positioned on the glove surface itself to lie above the area between the thumb and index finger on the dorsal side of the hand, however receptacle affixation allows placement in any location suitable to the user. A peel-off cover protects the patch until immediatelY prior to use.

The receptacle structure may also be affixed to the glove surface by means of a user applied adhesive stored in a tube, a hook and pile fastening system, a snap-on fastener, or a tongue-in-groove configuration.

In its simplest form, the recePtacle may simplY be a well upon the exposed surface of the glove itself. After donning the glove, the user may load the well with an appropriate amount of paste. An invagination or pouch on the glove surface may also be utilized as the storage receptacle. A puckering of the glove surface using hand motions or a spreading of the pouch cover members will expose the paste for convenient administration My invention described above provides a simple appliance for administering dental supplies from the surface of latex gloves. The appliance permits user access to the supplies from any position on the glove surface, thereby assuring convenient administration The glove and attached supply receptacle may subsequently be removed for disposal. My invention partially negates the loss of dexterity caused by the mandatory use of latex gloves in dental practice. The appliance also expedites a tedious dental procedure and aids the dental practitioner in efficient utilization of time,

BRIEF DESCRIPTION OF THE DRAWINGS

FIG. 1 is a perspective view of the apparatus with the receptacle structure affixed to the dorsal glove surface;

FIG. 2 is a sectional view of the receptacle structure in an embodiment utilizing an adhesive patch as means for attachment to the glove surface;

FIG. 3 is an alternate embodiment utilizing a hook and pile means for attachment;

FIG. 4 is another alternate embodiment utilizing snap or tongue-in-groove means for attachment;

FIG. 5 is Yet another embodiment utilizing a depression on the glove surface as a receptacle; and FIG. 6 is still another embodiment utilizing a pouch on the glove surface as a receptacle.

DESCRIPTION OF A PREFERRED EMBODIMENT

Referring to FIG. 1, my inventIon Is an apparatus for dispensing dental supplies which is used in conjunction with a latex barrier glove 11. Receptacle structure 12 is shown affixed to the dorsal surface of glove 11, supported by the web of the user's hand between the thumb and index finger. However, it should be noted that receptacle structure 12 may be attached at any location on the glove surface. Cup-like receptacle 13 retains cleaning agent 14 Adhesive patch 16 mounts on base 17 and bonds receptacle structure 12 to the surface of glove 11.

FIG. 2 shows an embodiment of receptacle structure 12 prior to attachment to glove 11 Coverlet 18 adheres to the upper rim of receptacle 13 and stretches over the opening thereof to maintain the sterility of cleaning agent 14. Receptacle 13 attaches to the upper surface of base 17. Adhesive patch 16 mounts on the lower surface of base 17. Protective cove 19 maintains the adhesive properties of patch 16 and is removed immediately prior to attachment of receptacle structure 12 to glove 11.

FIGS. 3 and 4 depict alternate embodiments of the present invention. In each, a different means for attachment replaces adhesive patch 16. In FIG. 3, hooks 21 mounted on base 17 interact with piles 22 mounted on the surface of glove 11. FIG. 4 shows a protuberance 23 extending downward from base 17 which cooperates with an aperture in a platform 24 attached to the surface of glove 11.

FIG. 5 shows a cup-like receptacle 26 molded directly into the surface of the glove 11. After donning the gloves, the user may load the receptacle 26 with the cleaning agent 14 for subsequent administration to the patient. After completion of the procedure the glove may easilly be removed for disposal.

In FIG. 6 a pouch 27 is molded into the surface of the glove 11. A pair of molded overlaping members 28 coorperate to form a receptacle for the cleaning agent 14. The cleaning agent may be pre-packaged in the pouch 27 or may be loaded from a bulk jar after the donning of the gloves. Stored cleaning agent in the pouch 27 may be exposed by spreading apart the overlapping members 28. Thumb and forefinger motions spread apart or pucker the overlapping members 28 to allow access to the retained cleaning agent A suitably configured pouch may also be used for retention of dental instruments. The instruments may easily be inserted prior to performance of the dental procedure and thereafter removed when needed Glove and pouch are easliy removed for disposal.

It will also be appreciated that other suPPlies such as sponges or sutures and the like maY be conveniently affixed to the dorsal side of a glove and thus become readily available to personnel in a variety of medical settings such as operating rooms or emergency rooms or ambulances.

What I claim is:

1. An appliance for holding medical supplies such as instruments or medication during dental procedures comprising:
    (a) glove means for covering the hand and wrist of the user forming a barrier about the hand of the user; and
    (b) a deformable cup-like receptacle of sufficient size to contain a predetermined dose of said medical supplies on the surface of said glove means for releaseably securing said medical supplies such that they may be selectively removed therefrom by user.

2. An appliance as defined in claim 1 wherein said glove means is a latex barrier glove.

3. An appliance as defined in claim 2 wherein said cup-like receptacle is molded on the exposed surface of the glove.

4. An appliance as defined in claim 2 wherein said cup-like receptacle further comprises a detachable coverlet sealing said receptacle to prevent contamination of the dental supplies contained therein.

5. An appliance for holding medical supplies such as instruments or medicants during dental procedures comprising:
    (a) glove means for covering the hand and wrist of the user; and
    (b) a deformable cup-like receptacle of sufficient size to contain a predetermined dose of said medical supplies said receptacle is affixed on said glove means by a bonding adhesive deposited on said retention means.

6. An appliance for holding medical supplies such as instruments or medicants during dental procedures comprising:
    (a) glove means for covering the hand and wrist of the user; and
    (b) a deformable cup-like receptacle of sufficient size to contain a predetermined dose of said medical supplies said receptacle is affixed on said glove means by a hook and pile fastening system.

7. An appliance for holding medical supplies such as instruments or medicants during dental procedures comprising:
    (a) glove means for covering the hand and wrist of the user; and
    (b) a deformable cup-like receptacle of sufficient size to contain a predetermined dose of said medical supplies said retention means having a projection thereon for interlocking engagement with a platform mounted on said glove means.

8. An appliance for holding medical supplies such as instruments or medicants during dental procedures comprising:
    (a) glove means for covering the hand and wrist of the user; and
    (b) a deformable cup-like receptacle of sufficient size to contain a predetermined dose of said medical supplies said receptacle is affixed on said glove means by a flat, compressible patch, the exposed surface of said patch being impregnated with a bonding adhesive.

9. An appliance as defined in claim 8 wherein the exposed surface of said patch is overlain by a detachable cover to preserve the adhesive impregnated thereon.

10. A device for dispensing supplies during medical procedures comprising:
    (a) a latex glove covering the hand of the user;
    (b) an enclosure for containing said supplies; and
    (c) means for detachably affixing said enclosure to the surface of said glove.

11. A device as defined in claim 10 wherein said enclosure comprises:
    (a) an open, concave vessel for stowage of prophylaxis paste;
    (b) a removable coverlet stretched over the opening of said vessel to prevent contamination of said paste; and
    (c) a flat supporting base affixed to the underside of said vessel.

12. A device as defined in claim 11 wherein said means for detachably affixing comprises an adhesive strip attached to the underside of said base or the surface of said glove; said strip being protected by a removable cover on the exposed surface thereof.

13. An apparatus as defined in claim 12 wherein said vessel and base are constructed of deformable material such that said glove is more easily removable when said enclosure is affixed thereto.

14. A device as defined in claim 11 wherein said means for detachably affixing comprises a hook and pile fastener.

15. A device as defined in claim 11 wherein said means for detachably affixing is an adhesive deposited on said enclosure.

16. A device as defined in claim 11 wherein said means for detachably affixing comprises means for interlocking engagement between said glove and said enclosure.

* * * * *